US008700127B2

(12) United States Patent (10) Patent No.: US 8,700,127 B2
Salerno et al. (45) Date of Patent: Apr. 15, 2014

(54) MOTION-ATTENUATED CONTRAST-ENHANCED CARDIAC MAGNETIC RESONANCE IMAGING SYSTEM AND METHOD

(75) Inventors: Michael Salerno, Charlottesville, VA (US); Frederick H. Epstein, Charlottesville, VA (US); Christopher M. Kramer, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 472 days.

(21) Appl. No.: 12/696,433

(22) Filed: Jan. 29, 2010

(65) Prior Publication Data

US 2010/0191099 A1 Jul. 29, 2010

Related U.S. Application Data

(60) Provisional application No. 61/148,249, filed on Jan. 29, 2009.

(51) Int. Cl.
*A61B 5/055* (2006.01)
(52) U.S. Cl.
USPC ............................................. 600/420; 600/413
(58) Field of Classification Search
USPC .................. 600/410, 413, 419, 420
See application file for complete search history.

(56) References Cited

U.S. PATENT DOCUMENTS

| 5,000,182 | A  | * | 3/1991 | Hinks ........................... 600/413 |
| 6,804,546 | B1 | * | 10/2004 | Thompson et al. ........... 600/410 |
| 8,072,215 | B2 | * | 12/2011 | Fuderer ........................ 324/318 |
| 2003/0100827 | A1 | * | 5/2003 | Deimling ...................... 600/410 |
| 2008/0242973 | A1 | * | 10/2008 | Warmuth ...................... 600/413 |
| 2009/0005673 | A1 | * | 1/2009 | Rehwald et al. .............. 600/420 |
| 2010/0063380 | A1 | * | 3/2010 | Duerk et al. .................. 600/410 |

* cited by examiner

*Primary Examiner* — Ruth S Smith
(74) *Attorney, Agent, or Firm* — Troutman Sanders LLP; Ryan A. Schneider; Christopher W. Glass

(57) ABSTRACT

A system and method for providing a dark-blood technique for contrast-enhanced cardiac magnetic resonance, improving visualization of subendocardial infarcts or perfusion abnormalities that may otherwise be difficult to distinguish from the bright blood pool. In one technique the dark-blood preparation is performed using a driven-equilibrium fourier transform (DEFT) preparation with motion sensitizing gradients which attenuate the signal in the ventricular cavities related to incoherent phase losses resulting from non-steady flow within the heart. This dark-blood preparation preserves the underlying contrast characteristics of the pulse sequence causing a myocardial infarction to be bright while rendering the blood pool dark. When applied to perfusion imaging, this dark-blood preparation will help eliminate artifacts resulting from the juxtaposition of a bright ventricular cavity and relatively dark myocardium.

26 Claims, 10 Drawing Sheets

MS-Prep dark-blood scheme

IR-FLASH

**IR FLASH
with MS-Prep**

MOTION-ATTENUATED CONTRAST-ENHANCED CARDIAC MAGNETIC RESONANCE IMAGING SYSTEM AND METHOD

RELATED APPLICATIONS

This application claims the benefit of priority of U.S. Provisional Application Ser. No. 61/148,249, filed on Jan. 29, 2009, entitled "Motion-Attenuated Contrast-Enhanced Cardiac Magnetic Resonance Imaging and Related Method thereof; the disclosure of which is hereby incorporated by reference herein in its entirety.

FIELD OF THE INVENTION

The present invention is directed to an improved technique for magnetic resonance imaging (MRI). More specifically, aspects of the present invention are directed to techniques that improve contrast during cardiovascular magnetic resonance imaging by suppressing the blood pool signal, rendering the heart cavities dark and improving visualization of heart anatomic structures, scars in the heart, and myocardial perfusion.

BACKGROUND OF THE INVENTION

Coronary artery disease (CAD) affects millions of people and heart disease remains the number one cause of death worldwide. Given the importance and prevalence of this type of disease, there has been considerable interest in imaging techniques capable of diagnosing CAD. Cardiovascular magnetic resonance imaging (CMR) has emerged as an important imaging technique for evaluating CAD and other heart diseases. CMR involves the application of MRI principles optimized for use in the heart. CMR provides an image of the heart and can be used to detect abnormalities in function, blood flow, edema and the presence of myocardial infarction.

One important use of CMR in the evaluation of CAD is the identification of myocardial infarction, In recent years delayed contrast enhanced CMR techniques have enabled accurate quantification of myocardial infarction. For example, Kim et al. in U.S. Pat. No. 6,205,349 entitled "Differentiating normal living myocardial tissue, injured living myocardial tissue, and infarcted myocardial tissue in vivo using magnetic resonance imaging", describe a technique for distinguishing between normal and infracted myocardium using contrast enhanced CMR imaging. However, small subendocardial infarcts may be difficult to detect and quantify accurately as they may be obscured by the bright signal in the blood pool.

Another important use of CMR is myocardial perfusion imaging. Over the last few years, improvements in hardware, pulse sequence development, and image reconstruction algorithms have enabled high resolution imaging of the first pass of a gadolinium based contrast agent through the myocardium. This has become a methodology utilized in adenosine stress MRI to assess myocardial perfusion. One of the major limitations of current CMR perfusion imaging techniques is the dark-rim artifact. Normally, regions of decreased perfusion are subendocardial and appear dark on CMR perfusion images. The dark rim artifact is a dark region which appears at the subendocardial border of the myocardium and can be mistaken for a true perfusion defect, causing a false positive study likely resulting in further expensive and invasive diagnostic tests such as coronary angiography. This dark rim artifact results from the inherent motion of the heart, magnetic susceptibility differences between the blood pool and myocardium, and limitations to the spatial resolution resulting from rapid imaging. As the intensity of this artifact is related to the presence of a bright blood pool signal next to a darker myocardium, attenuating the signal from the blood pool using a motion-sensitized preparation will significantly reduce this type of artifact.

Both of these examples demonstrate applications where bright signal in the blood pool can reduce the diagnostic utility of CMR for evaluation of coronary artery disease. To overcome issues of bright blood signal in cardiovascular magnetic resonance imaging, multiple techniques have been developed to suppress signal from the blood pool. Foo et al. U.S. Pat. No. 6,498,946 describe a technique consisting of a non-slice selective radiofrequency (RF) inversion pulse and slice-selective re-inversion RF pulses (so called double inversion recovery (DIR)) combined with a turbo-spin-echo readout for dark blood anatomical imaging of the heart. Another paper in the public domain describes T2-relaxation weighted imaging with dark blood employing a similar pair of inversion pulses to null the blood pool (Simonetti et. al 1996). Similarly, there is prior art for using multiple RF inversion pulses for suppressing the blood signal for imaging the walls of blood vessels and for multi-slice imaging. (Fayad, et al., U.S. Pat. No. 7,369,887)

The above prior art refer to imaging of the signal of the protons without the addition of a contrast agent. A gadolinium based contrast can be administered which shortens the T1 relaxation of the protons and results in a bright signal in inversion recovery (IR) pulse sequences. The addition of a contrast agent makes blood suppression more difficult as the shorter relaxation times put higher demands on timing parameters and result in a shorter time for washout of the blood in the imaging slice. This results in incomplete suppression of the blood pool signal and causes image artifacts. Foo et al. (U.S. Pat. Nos. 6,662,037 and 6,526,307) describe a technique for nulling the signal from the blood pool by combining a "notched rf pulse" which effectively suppresses the blood signal outside of the slice of interest, and with blood flow in the heart this suppressed signal moves into the slice of interest and is rendered dark. This technique is susceptible to errors in the slice profile of the "notched" rf pulse as well as requiring all of the blood to move out of the slice to null the signal.

Two other techniques for suppressing the blood pool in contrast enhanced imaging of myocardial infarction have been described. Rehwald et al. (U.S. Patent Application Publication No. US 2009/0005673 A1 (Ser. No. 11/957,520)) have developed a technique based on the combination of a slice selective rf pulse and a non-selective rf pulse with precise timing which nulls the signal from the blood pool. While this technique greatly improves contrast between the blood pool and the infarct, it does so at an expense of signal-to-noise ratio and contrast-to-noise with respect to the normal myocardium. The technique also has some susceptibility to slow flowing blood and changes in the parameters as a function of the magnetic relaxation parameters of the heart. A pulse sequence by Ibrahim et al., which is based on the stimulated echo acquisition-mode (STEAM) technique, also has the ability to suppress the signal from the blood pool (Ibrahim et. al. 2008). However, this technique requires three separate images of the heart, and suffers from STEAM's inherent 50% decrease in SNR.

A different method for suppressing the signal from the blood relies on phase dispersion related to the inherent self-diffusion coefficient of water. This idea was first described for suppressing the blood signal for imaging of the brain with a so called "arterial-spin labeling" technique (Pell et al. 2003). This concept was extended to contrast enhanced vessel wall imaging (Koktzoglou et. al. 2007). In this technique a diffusion prepared driven-equilibrium fourier transform (DEFT) preparation is used consisting of a 90 degree rf pulse followed by a strong magnetic field gradient, then followed by a 180 degree pulse another magnetic field gradient and finally a negative 90 degree pulse to null the blood signal based on the high self diffusion coefficient of water ($2.2 \times 10-3$ mm$^2$/s). In both of these applications large gradients are played out resulting in diffusion attenuation coefficients (b-values) of 0.7 s/mm$^2$. Very recently, this concept has been extended to non-contrast imaging of the heart combining a DEFT preparation with a steady-state free procession readout scheme (Nguyen et al. 2008).

However, none of the current techniques apply motion-sensitized dark-blood techniques for imaging of first-pass perfusion or delayed enhancement of the myocardium with gadolinium-based contrast agents.

SUMMARY OF THE INVENTION

An aspect of an embodiment of the present invention provides a method for attenuating the signal from the blood pool, particularly for contrast-enhanced imaging applications including imaging of myocardial infarction and abnormalities in myocardial perfusion.

An aspect of an embodiment of the present invention provides a dark-blood technique for contrast-enhanced cardiac magnetic resonance, improving visualization of subendocardial infarcts or perfusion abnormalities that may otherwise be difficult to distinguish from the bright blood pool. In one implementation of an embodiment of the invention, the dark-blood preparation is performed using a driven-equilibrium fourier transform (DEFT) preparation with motion sensitizing gradients which attenuate the signal in the ventricular cavities related to incoherent phase losses resulting from non-steady flow within the heart. This dark-blood preparation preserves the underlying contrast characteristics of the pulse sequence causing a myocardial infarction to be bright while rendering the blood pool dark. When applied to perfusion imaging, this dark-blood preparation will help eliminate artifacts resulting from the juxtaposition of a bright ventricular cavity and relatively dark myocardium.

An aspect of an embodiment of the present invention involves the combination of an inversion rf pulse to impart post-gadolinium delayed enhancement contrast to the myocardium and a DEFT preparation with motion sensitization gradients to suppress the blood signal in the ventricular cavity. As the motion in the heart cavity has non-steady flow characteristics, an aspect of an embodiment of the invention involves the application of small gradients to suppress the signal from the ventricular cavity. Furthermore the timing of our preparation has been optimized to prevent loss of signal in the myocardial wall resulting from strain. This is a problem that specifically applies to imaging of the heart. Additionally, applying these techniques for contrast enhancement requires careful timing, as applying the DEFT preparation in certain configurations will result in a brighter, rather than darker blood pool signal.

While other techniques have been used to suppress the blood signal the technique associated with aspects of an embodiment of present invention has advantages over these known techniques. The other techniques which suppress the blood signal based on its T1 relaxation properties require precise knowledge of the T1 relaxation time of the blood pool and myocardium which are increasing continuously after the administration of gadolinium contrast. The motion sensitive preparation associated with aspects of an embodiment of the present invention is only dependent on the incoherent motion of the blood pool in the ventricular cavity to suppress the signal from the blood pool. Other techniques are dependent on the movement of blood out of the imaging plane prior to image acquisition, whereas motion-sensitive preparation of an embodiment of the present invention does not require movement of blood out of the imaging plane for adequate blood suppression. Finally, motion sensitive preparation of an embodiment of the present invention preserves the excellent contrast properties of IR-FLASH, and is robust to changes in T1 of the blood, and myocardium.

Another aspect of an embodiment of the present invention involves, but not limited thereto, the combination of a DEFT preparation with first-pass contrast-enhanced perfusion imaging of the heart. Conventional techniques do not apply motion-sensitization techniques to imaging of first-pass perfusion with gadolinium-based contrast agents. This aspect of an embodiment of the present invention involves the use of motion-sensitizing techniques in combination with first pass-perfusion techniques to mitigate the dark-rim artifact. As the intensity of the dark-rim artifact is related to the difference in intensity of the bright blood pool and darker myocardium, attenuating the blood pool signal may eliminate this type of artifact. Suppression of the dark-rim artifact during contrast-enhanced first-pass perfusion imaging is not a characteristic of any conventional techniques and should improve the diagnostic accuracy of myocardial perfusion imaging techniques. This is especially important, for example, as false positive stress myocardial perfusion studies frequently result in patients undergoing additional expensive and invasive diagnostic procedures such as coronary angiography.

An aspect of an embodiment of the present invention provides a method for magnetic resonance imaging of a heart of a subject. The method may comprise: administering a contrast agent to the subject; applying a nuclear magnetic resonance preparation to impart contrast weighting to the heart; applying a motion-sensitization preparation to modulate a signal corresponding to blood within the heart; and reading out a nuclear magnetic resonance signal from the heart. Reading out the nuclear magnetic resonance signal from the heart may comprise: gradient echo or gradient echo-train readout; spin echo or turbo spin echo readout; or a combination of spin echoes and gradient echo readouts.

An aspect of an embodiment of the present invention provides a method for magnetic resonance imaging of a heart of a subject. The method may comprise: applying a nuclear magnetic resonance preparation to impart contrast weighting to the heart; applying a motion-sensitization preparation to modulate a signal corresponding to blood within the heart; and reading out a nuclear magnetic resonance signal from the heart. Reading out the nuclear magnetic resonance signal from the heart may comprise: gradient echo or gradient echo-train readout; spin echo or turbo spin echo readout; or combination of spin echoes and gradient echo readouts.

An aspect of an embodiment of the present invention provides a method for magnetic resonance imaging of a heart of a subject. The method may comprise: applying a nuclear magnetic resonance preparation comprised of a plurality of rf-pulses and a plurality of magnetic field gradients to impart T1, T2, or T2* contrast weighting to the heart; applying a motion-sensitization preparation comprised of a plurality of rf-pulses and a plurality of magnetic field gradients to modulate a signal corresponding to a blood pool within the heart; and reading out a nuclear magnetic resonance signal from the heart.

An aspect of an embodiment of the present invention provides a system for magnetic resonance imaging of a heart of a subject. The system may comprise: a data acquisition and display computer; a control sequencer; a MRI subsystem; and a display. The control sequencer may be programmed to: apply a nuclear magnetic resonance preparation comprised of a plurality of rf-pulses and a plurality of magnetic field gradients to impart T1, T2, or T2* contrast weighting to the heart; and apply a motion-sensitization preparation comprised of a plurality of rf-pulses and a plurality of magnetic field gradients to modulate a signal corresponding to a blood pool within the heart; and reading out a nuclear magnetic resonance signal from the heart.

An aspect of an embodiment of the present invention provides a system for magnetic resonance imaging of a heart. Accordingly, the system and related operation of an embodiment: applies a nuclear magnetic resonance preparation comprised of a plurality of rf-pulses and a plurality of magnetic field gradients to impart T1, T2, or T2* contrast weighting to the heart; applies a motion-sensitization preparation comprised of a plurality of rf-pulses and a plurality of magnetic field gradients to modulate a signal corresponding to a blood pool within the heart; and reads out a nuclear magnetic resonance signal from the heart.

The invention itself, together with further objects and advantages, will best be understood by reference to the following detailed description in conjunction with the accompanying drawings.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF THE INVENTION

MRI System

Figure 1:
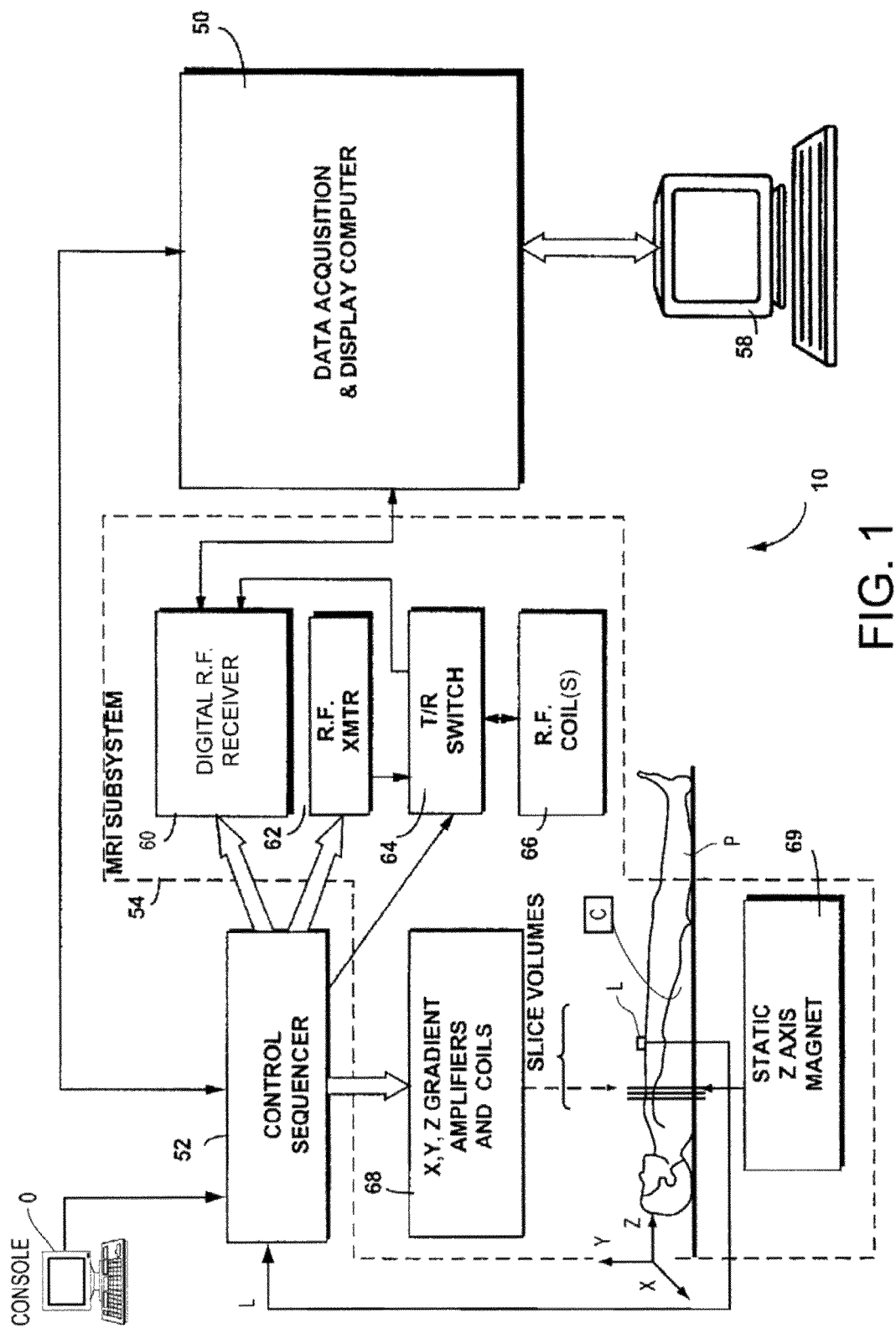
FIG. 1 schematically illustrates an example of an MRI system upon which an embodiment of the present invention could be implemented.

An embodiment of the present invention may be implemented on any commercial MRI system without necessarily requiring any additional hardware. FIG. 1 illustrates an example such MRI system 10 including a data acquisition and display computer 50 coupled to an operator console 0, a MRI real-time control sequencer 52, and a MRI subsystem 54. The MRI subsystem 54 may include XYZ magnetic gradient coils and associated amplifiers 68, a static Z-axis magnet 69, a digital RF transmitter 62, a digital RF receiver 60, a transmit/receive switch 64, and RF coil(s) 66. A dedicated phased-array coil and Electrocardiogram (ECG) leads L may be used for cardiac applications for synchronization of the control sequencer 52 with the electrical signals of the heart of patient P. The MRI Subsystem 54 may be controlled in real time by control sequencer 52 to generate magnetic and radio frequency fields that stimulate nuclear magnetic resonance ("NMR") phenomena in a patient P (e.g., a human body) to be imaged. A contrast agent C, such as Gd-DTPA for example, is injected intravenously into the patient P. A resulting contrast-enhanced image of the cardiac structures of patient P may be shown on display 58. Display 58 may be implemented through a variety of output interfaces, including a monitor, printer, or data storage.

Infarction Imaging

Figure 2A:
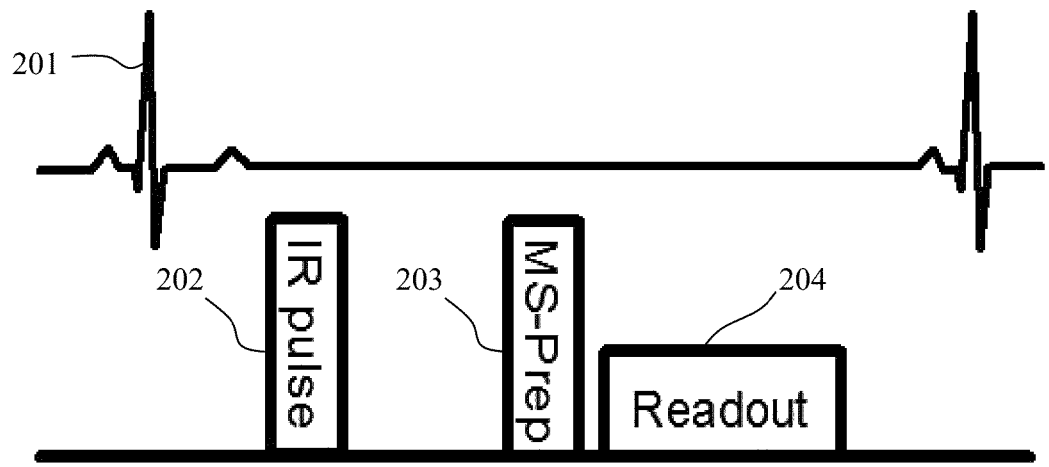
FIG. 2(A) illustrates an infarct imaging pulse sequence schematic.
Figure 2B:
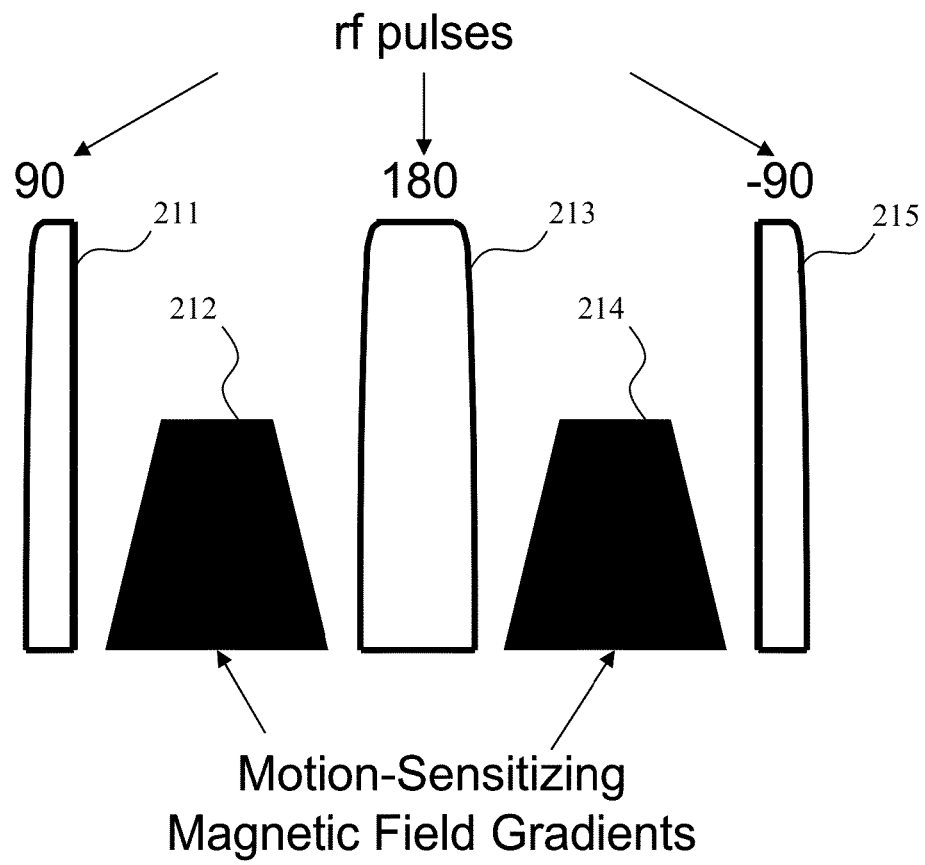
FIG. 2(B) illustrates the pulse sequence schematic of the motion-sensitization preparation (MS-Prep) in FIG. 2(A).

One aspect of an embodiment of the present invention, for attenuating the blood signal in a ventricular cavity to improve contrast between myocardial infarction, scar, or fibrosis, is demonstrated in FIG. 2(A) and FIG. 2(B). A pulse sequence is played out on the real-time control sequencer 52 with specific timing of magnetic field gradients and rf-pulses to create a post-contrast image of the heart where scar appears bright, and both the blood pool and the normal myocardial signal is depressed. The timing of the inversion-recovery (IR) rf-pulse 202 is synchronized to a fixed delay after the ECG trigger 201, as depicted in FIG. 2(A). The inversion-recovery rf-pulse 202 imparts T1 contrast weighting by inverting all of the magnetization within the patient P. Those skilled in the art will readily understand that other nuclear magnetic resonance preparations and contrast weightings may be used, such as T2, T2*, or any other contrast weighting used in MRI.

Once the magnetization from the blood pool has recovered past its null point, the motion-sensitization preparation 203, depicted in detail in FIG. 2(B), may be played out by the real-time control sequencer 52. The motion-sensitization preparation 203 in this aspect may, for example, comprise multiple steps.

First, an rf-pulse 211 is played out with the intent of creating transverse magnetization. The total flip angle of this rf-pulse is typically 90 degrees.

Second, a magnetic field gradient pulse 212 is played out by one or more of the XYZ magnetic gradient coils and associated amplifiers 68. This creates a dispersion of phase angles of spin isochromats which will lead to attenuation in the presence of motion.

Third, a refocusing rf-pulse 213 is played out to refocus effects of magnetic field inhomogenieties.

Fourth, another magnetic field gradient pulse 214 is played out.

Finally, an rf-pulse 215 is played to restore the residual transverse magnetization to longitudinal magnetization.

It will be appreciated by those skilled in the art that any of the rf-pulses 211, 213, or 215 can be accomplished through a single rf-pulse, a component of a composite rf-pulse, or a series of rf-pulses played in rapid succession.

The net effect of motion-sensitizing preparation 203 is to attenuate the signal from the blood pool. Motion-sensitizing preparation 203 has very little effect on stationary tissues like the myocardium but a significant effect upon the turbulent blood, suppressing the signal corresponding to the blood pool. With the proper timing, this results in a darker blood pool. Following the motion preparation, a suitable readout module 204 consisting of rf-pulses and magnetic field gradients is played out to collect the data. The readout module 204 is played out at a time when the magnetization from the normal myocardium is near or above its null point. Any suitable type of magnetic resonance imaging readout module can be used.

Figure 3A:
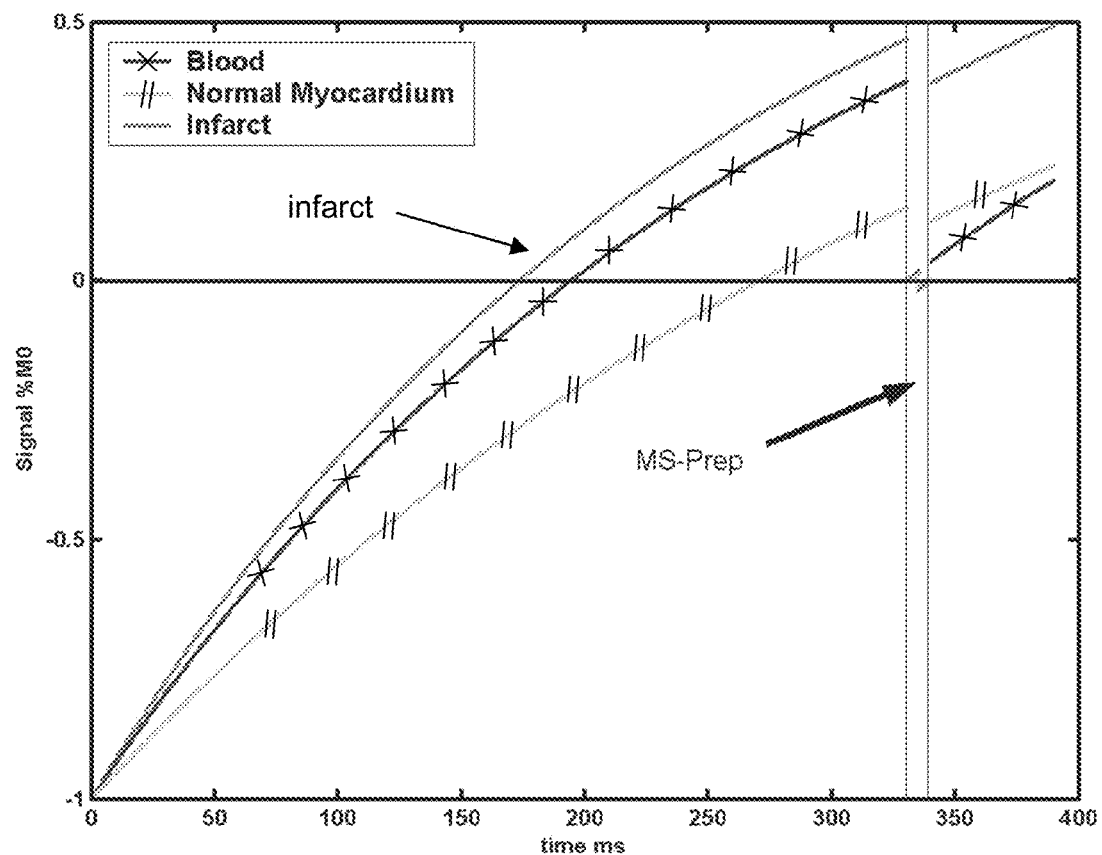
FIG. 3(A) illustrates the relaxation curves from the infarct imaging pulse sequence of FIG. 2(A).

FIG. 3(A) shows the transverse magnetization during the above-described aspect of the present invention. At time 0 an inversion recovery rf-pulse 202 is applied which inverts the magnetization. The magnetization of the blood, myocardium, and infarct recover with their respective T1 relaxation times. As the blood and infarct have short T1 relaxation times they recover rapidly. When the blood signal has recovered past the zero point, the motion-sensitization preparation 203 is played out. This primarily attenuates the signal from the blood pool, but also slightly attenuates signal from the myocardium and the infarct. At a suitable time when the myocardial signal has recovered past its null point the readout module 204 can be played out. The timing from the inversion recovery rf-pulse 202 to the readout pulse sequence module 204 is chosen so that the signal from the normal myocardium will be near but above the null point. This time is referred to as TI.

Figure 3B:
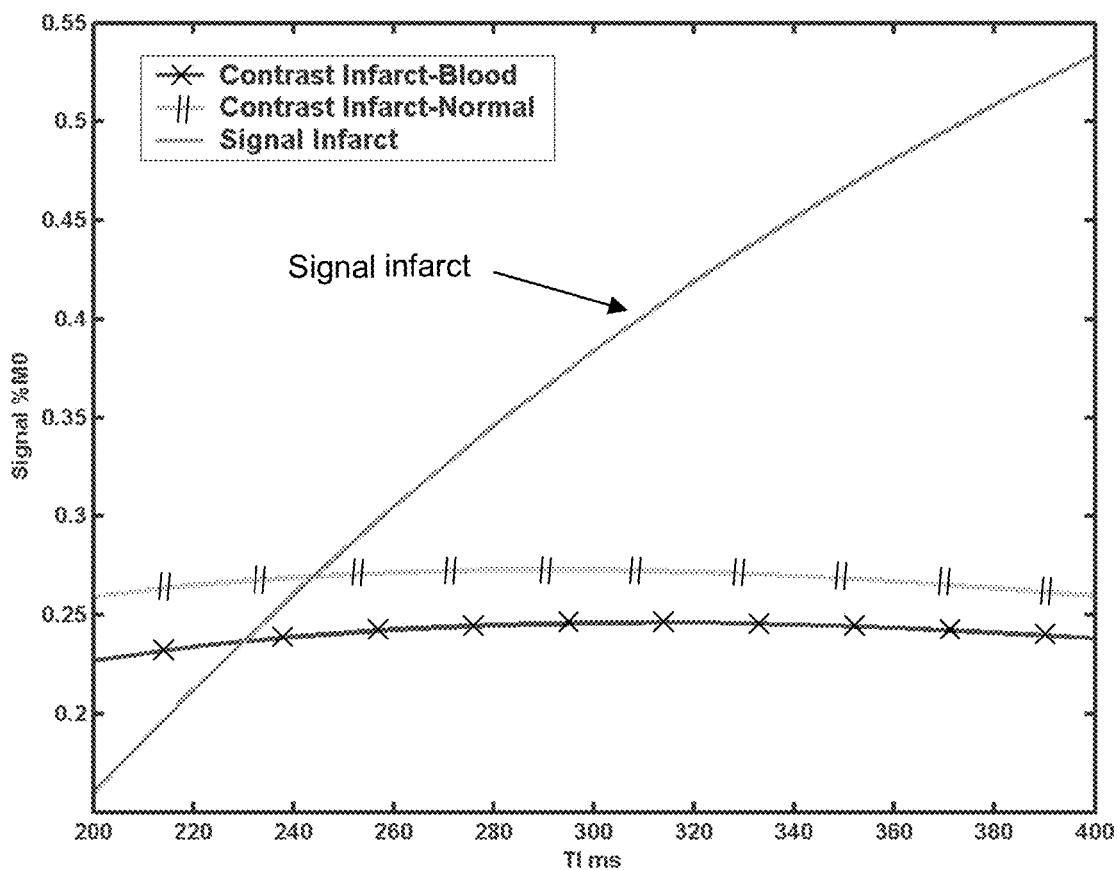
FIG. 3(B) illustrates the contrast curves from of the infarct imaging pulse sequence of FIG. 2(A).

FIG. 3(B) demonstrates the difference in signal intensity (contrast) between both the infarct and normal myocardium (shown as "contrast infarct-Normal") and the infarct and blood (shown as "contrast infarct-Blood"). Note that these contrast curves are fairly flat for a range of TI times. The figure also shows (shown as "Signal infarct") that the signal from infarcted myocardium or scar continues to increase as TI is increased, which leads to a higher signal-to-noise (SNR) ratio for the infarct as TI is increased.

Figure 4A:
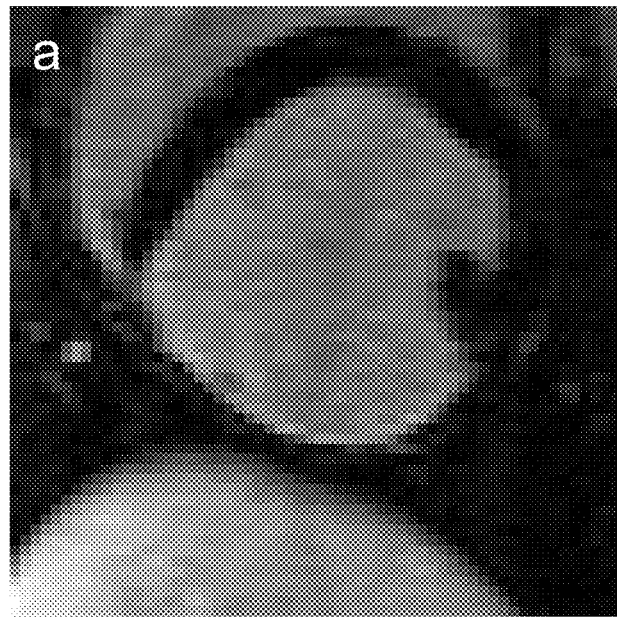
FIGS. 4(A) and 4(B) demonstrate comparison images of the conventional technique and of an embodiment of the present invention's dark-blood infarct imaging techniques, respectively.
Figure 4B:
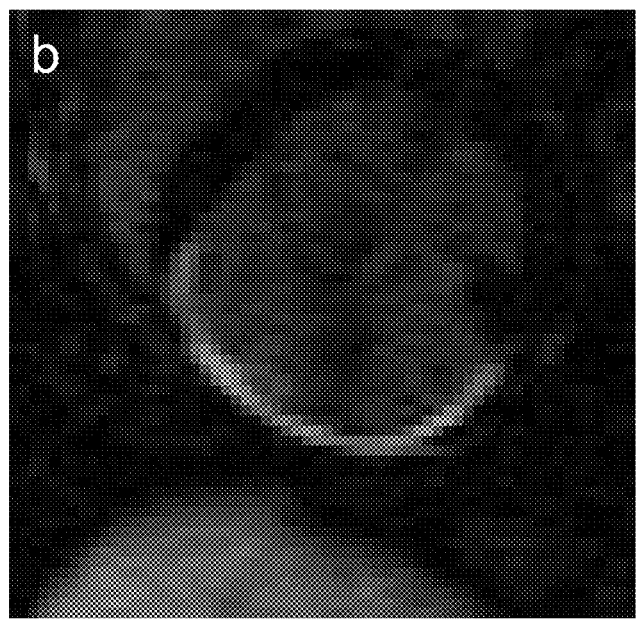

FIG. 4 demonstrates an example of images obtained with FIG. 4(A) as the conventional bright-blood IR-FLASH delayed enhancement imaging pulse sequence and FIG. 4(B) as the motion-sensitized dark-blood delayed enhancement pulse sequence, as depicted in FIG. 2(A) and FIG. 2(B), respectively. These example images were obtained on a commercial 1.5 T magnetic resonance scanner in a canine subject with chronic myocardial infarction. Imaging was performed about 5-10 minutes after injection of 0.15 mg/kg of Gd-DTPA (Magnevist). Sequence parameters included: field of view—300 mm; matrix—192×114; TE—2.7 ms; spatial resolution—1.6×2.3×10 mm; lines per segment—12; bandwidth—400 Hz/pixel; acquisition duration—16 heartbeats.

The motion-sensitization preparation 203 in this example (image of FIG. 4(B)) is composed of a BIR-4 composite rf-pulse consisting of 3 components: a 90 degree pulse, a 180 degree pulse, and a negative 90 degree pulse. Unipolar magnetic field gradients are applied in the thru-plane direction with amplitude of 20 mT/m and a duration of 1 ms each on either side of the 180 degree pulse (see FIG. 3). The effective b-value (diffusion attenuation coefficient) was 0.25 s/mm^2. In the image as shown in FIG. 4(A), the image obtained with the conventional pulse sequence (no dark-blood preparation), the infarct in the inferior wall is not easily distinguished from the blood pool. In the image as shown in FIG. 4(B), the dark-blood pulse sequence image, the infarct-blood pool border is clearly visible. The b-value used for imaging the myocardial cavity is generally smaller than that for vessel wall imaging. Furthermore, the quicker recovery times when contrast is given, and inherent strain (contraction) of the heart require shortening the timing of the preparation.

Contrast-Enhanced First-Pass Imaging of Myocardial Perfusion

Figure 5:
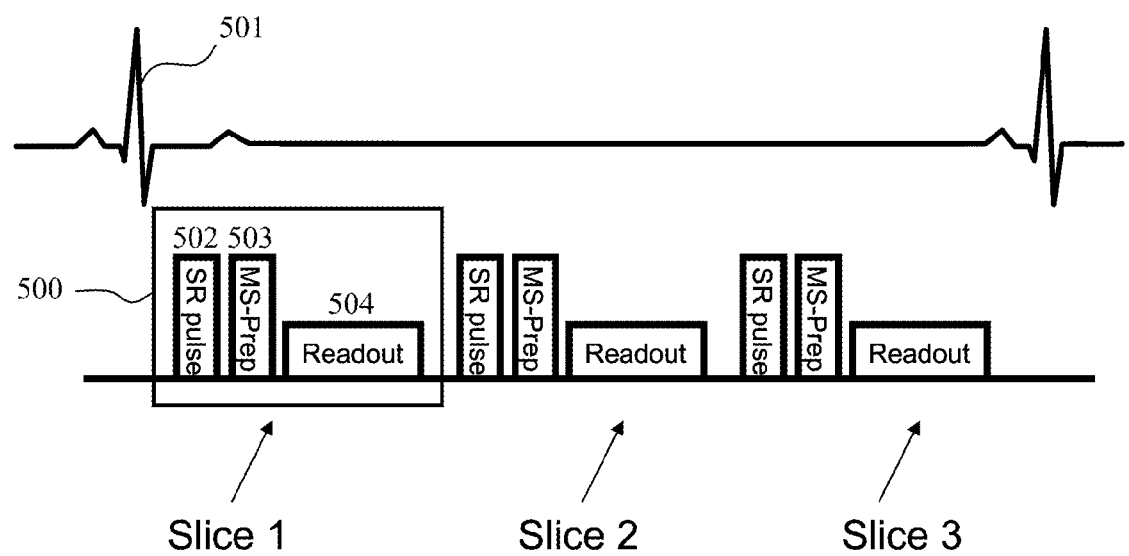
FIG. 5 illustrates a dark-blood perfusion imaging pulse sequence schematic.

An aspect of an embodiment of the present invention for attenuating the blood signal in a ventricular cavity to improve contrast and eliminate dark-rim artifacts for first-pass contrast-enhanced imaging of the heart is demonstrated in FIG. 5. A pulse sequence is played out on the real-time control sequencer 52 with specific timing of magnetic field gradients and rf-pulses to create an image where the signal from the blood pool is attenuated during first-pass perfusion. The timing of the pulse sequence for the first slice position is typically timed to the ECG 501. The same perfusion pulse sequence 500 is played out a number of times within each R-R interval of the ECG each at a different slice position to evaluate perfusion at multiple locations within the target ventricle. The perfusion pulse sequence 500 begins with a saturation recovery preparation module consisting of an rf-pulse, or combination of rf-pulses used to impart T1 weighting to the magnetization of the myocardium and blood pools. This is customarily, but not limited to a 90 degree pulse. A series of gradient pulses, SR rf-pulse 502, are applied to spoil the residual transverse magnetization following this preparation. At a suitable time prior to the beginning of a readout module 504, a motion-sensitization preparation 503 such as, but not limited to the one described in FIG. 2(B) is played out. This motion-sensitization preparation 503 attenuates the signal from the blood pool in proportion to its incoherent motion. Following motion-sensitization preparation 503, a suitable readout module 504 consisting of multiple rf-pulses and magnetic field gradients is performed. The magnetization preparation is compatible with any readout scheme. For perfusion imaging typically single-shot rapid imaging modules are utilized. The same pulse sequence 500 is applied to all of the slices each R-R interval during first pass of the contrast agent C. Given the rapid T1 relaxation time of blood during first-pass of a gadolinium contrast agent at peak concentration the blood pool signal is decreased but not completely suppressed. This however, should be adequate for suppression of certain dark-rim artifacts.

It should be apparent to one skilled in the art that many types of nuclear magnetic resonance preparations may be used and that the SR rf-pulse 502 may be accomplished through a single rf-pulse, a component of a composite rf-pulse, or a series of rf-pulses played in rapid succession. Furthermore it should be apparent that the motion sensitized preparation is compatible with other contrast preparations schemes aimed at imparting T1, T2, T2*, or any other contrast weighting used in MRI.

Figure 6:
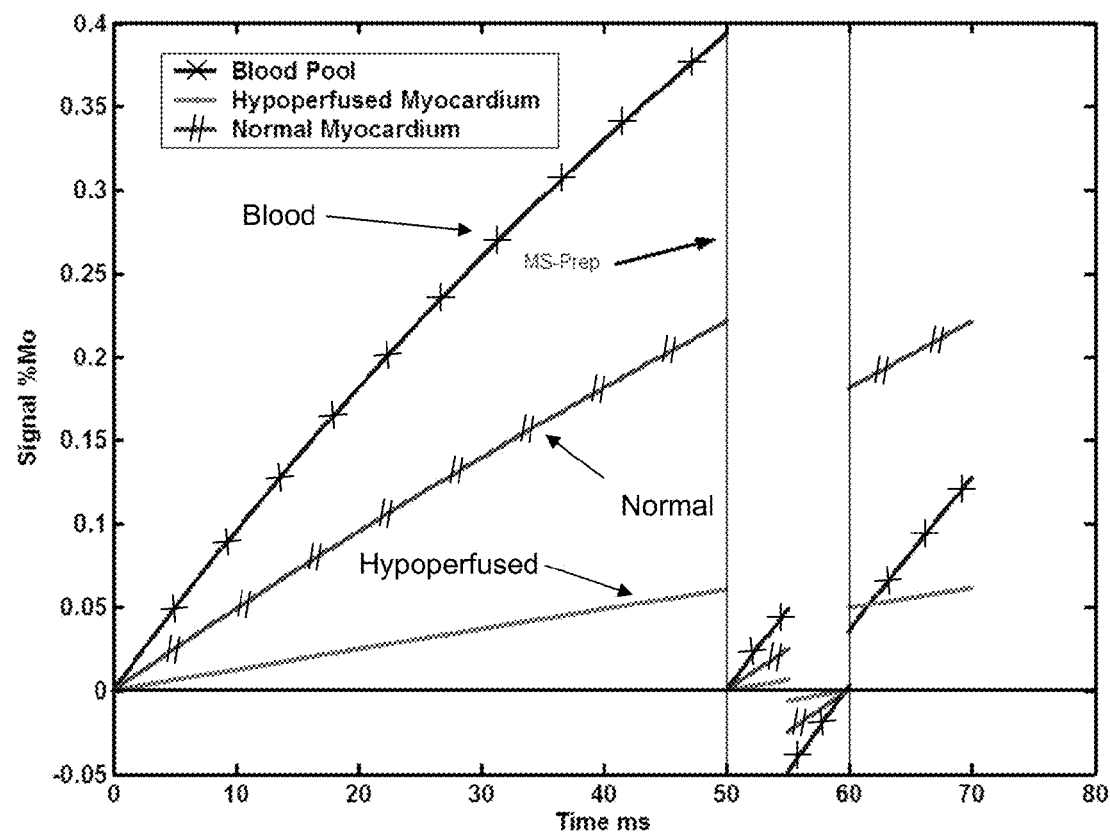
FIG. 6 illustrates relaxation curves from the perfusion imaging pulse sequence of FIG. 5.

FIG. 6 demonstrates magnetization relaxation curves for the above exemplary implementation of our method. The magnetization curves are representative of the relaxation times during first-pass perfusion imaging with a typical concentration of a gadolinium contrast agent. The application of SR pulse 502, a combination of rf-pulses totaling 90 degrees with gradient spoiling destroys the longitudinal and transverse magnetization of all species. As the blood pool has the shortest T1 relaxation time it recovers the fastest. Normal myocardium has an intermediate T1 and recovers slower, and hypoperfused myocardium has the longest T1 and recovers the slowest. Prior to the application of a readout module 504, the motion-sensitization preparation 503 is played out to attenuate the signal from the blood pool. During the readout the magnetization continues to recover, so the blood pool signal will have either a very low amplitude or amplitude intermediate to that of the normal and hypoperfused myocardium.

Figure 7:
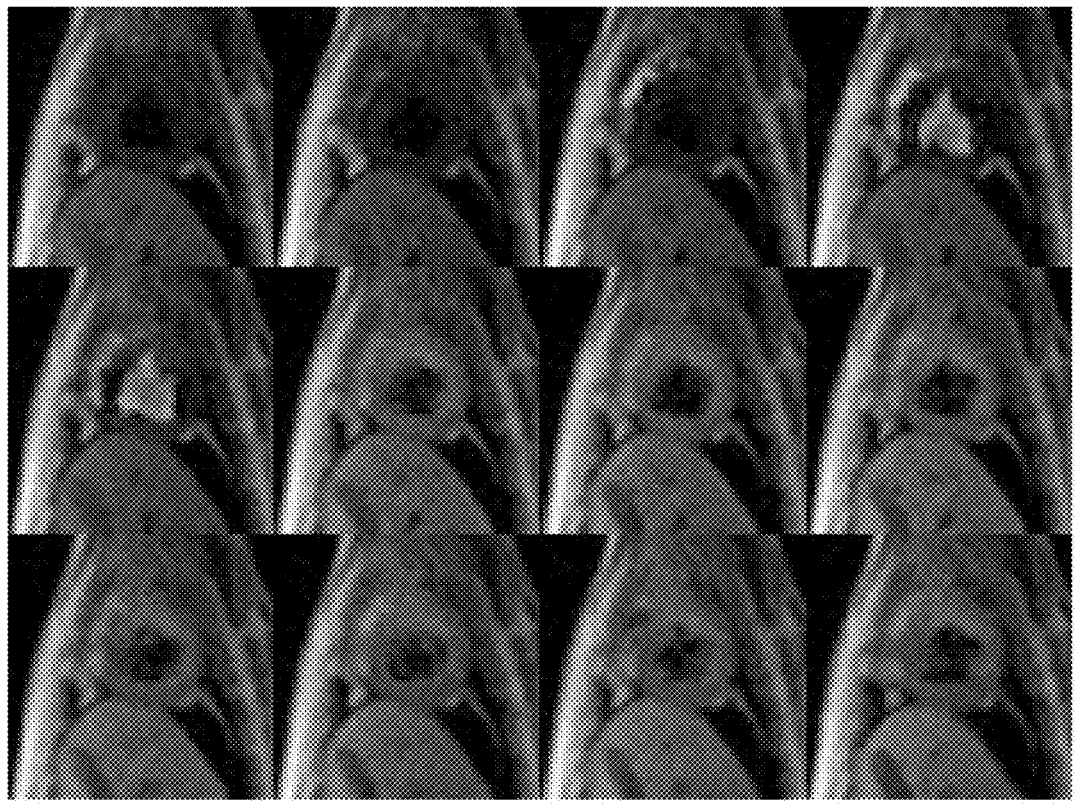
FIG. 7 demonstrates illustrative perfusion imaging using the motion-sensitized dark-blood imaging technique of an embodiment of the present invention.

FIG. 7 demonstrates example images obtained from the pulse sequence described herein during first-pass of a gadolinium-based contrast agents demonstrating attenuation of the blood pool signal. These example images were obtained on a commercial 1.5 T magnetic resonance scanner in a canine. Imaging was gated to the ECG and was performed continuously during injection of 0.075 mg/kg of Gd-DTPA (Magnevist). Images were obtained for 40 heartbeats during the first pass of the contrast agent. Sequence parameters included: FLASH gradient echo readout module; field of view—360×162 mm; matrix—160×54; TE 1.1 ms; spatial resolution—2.3×3×8 mm; bandwidth—650 Hz/pixel; acquisition duration per image—250 ms; saturation time—120 ms. The blood pool is completely suppressed within the ventricular cavity except for the time during peak blood-pool gadolinium concentration. The signal is completely suppressed by the preparation, but recovery of magnetization during the readout module results in a bright signal. Improved suppression of the blood pool signal will be achievable with more rapid readout modules.

Figure 8:
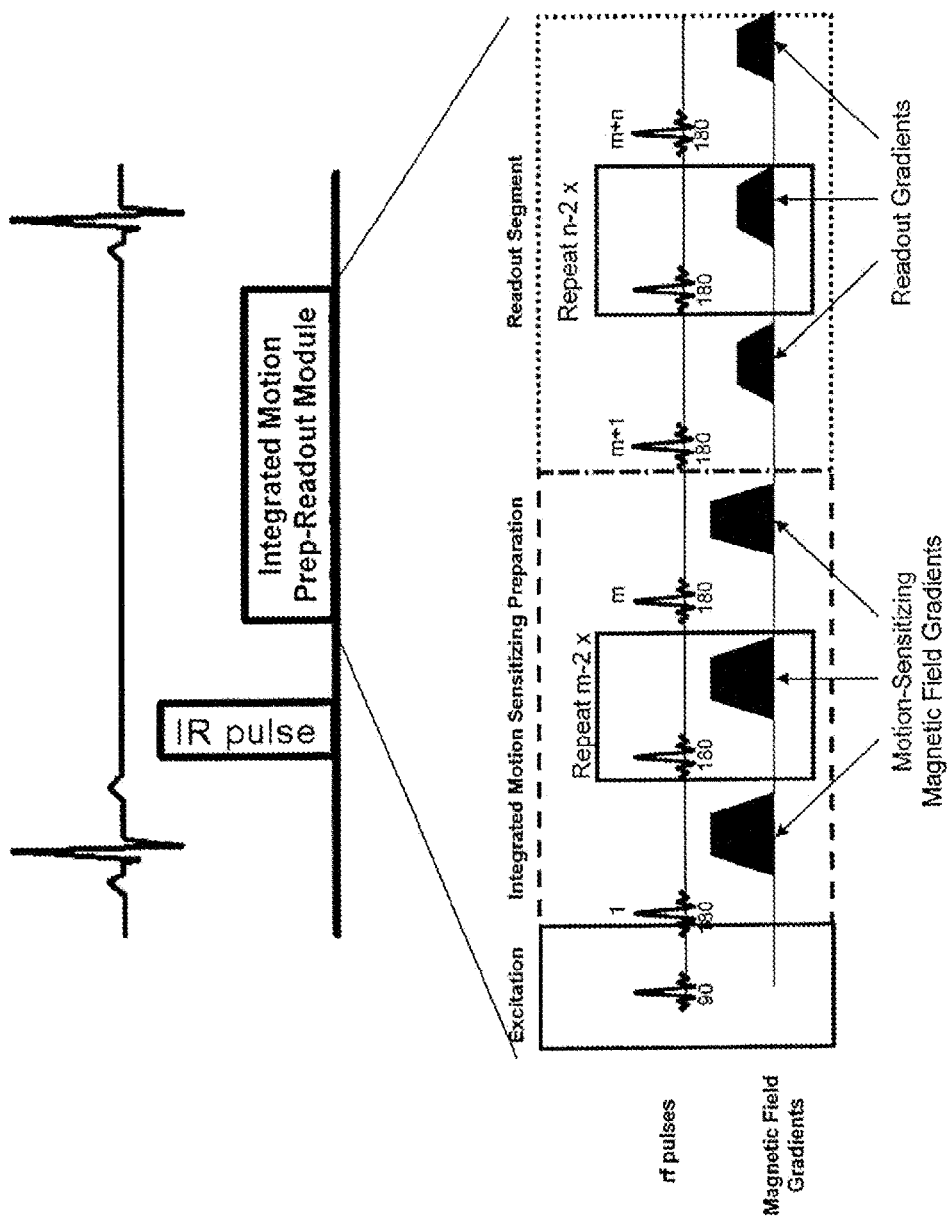
FIG. 8 illustrates integrating motion sensitization into a readout module, according to one aspect of an embodiment of the present invention.

FIG. 8 illustrates integrating motion sensitization into a readout module, according to one aspect of an embodiment of the present invention. An inversion or saturation pulse is applied to create desired $T_1$ weighting. Following the contrast preparation, a excitation pulse is applied (for example a 90 degree pulse), followed by a train of rf pulses (for example a 180 degree pulse) with a motion-sensitizing magnetic field gradient between each set of refocusing pulses. This is repeated m times, where m can be varied to achieve a desired amount of motion sensitization. Within the same train of refocusing modules following the motion sensitizing module, individual readouts are acquired within the same set of refocusing gradients which can be repeated n times. Thus, the motion sensitization and readout is performed in m+n intervals within a train of refocusing pulses after a single excitation pulse. The degree of T2 weighting can be determined by the location of the center of k-space acquisition during the readout train.

Figure 9:
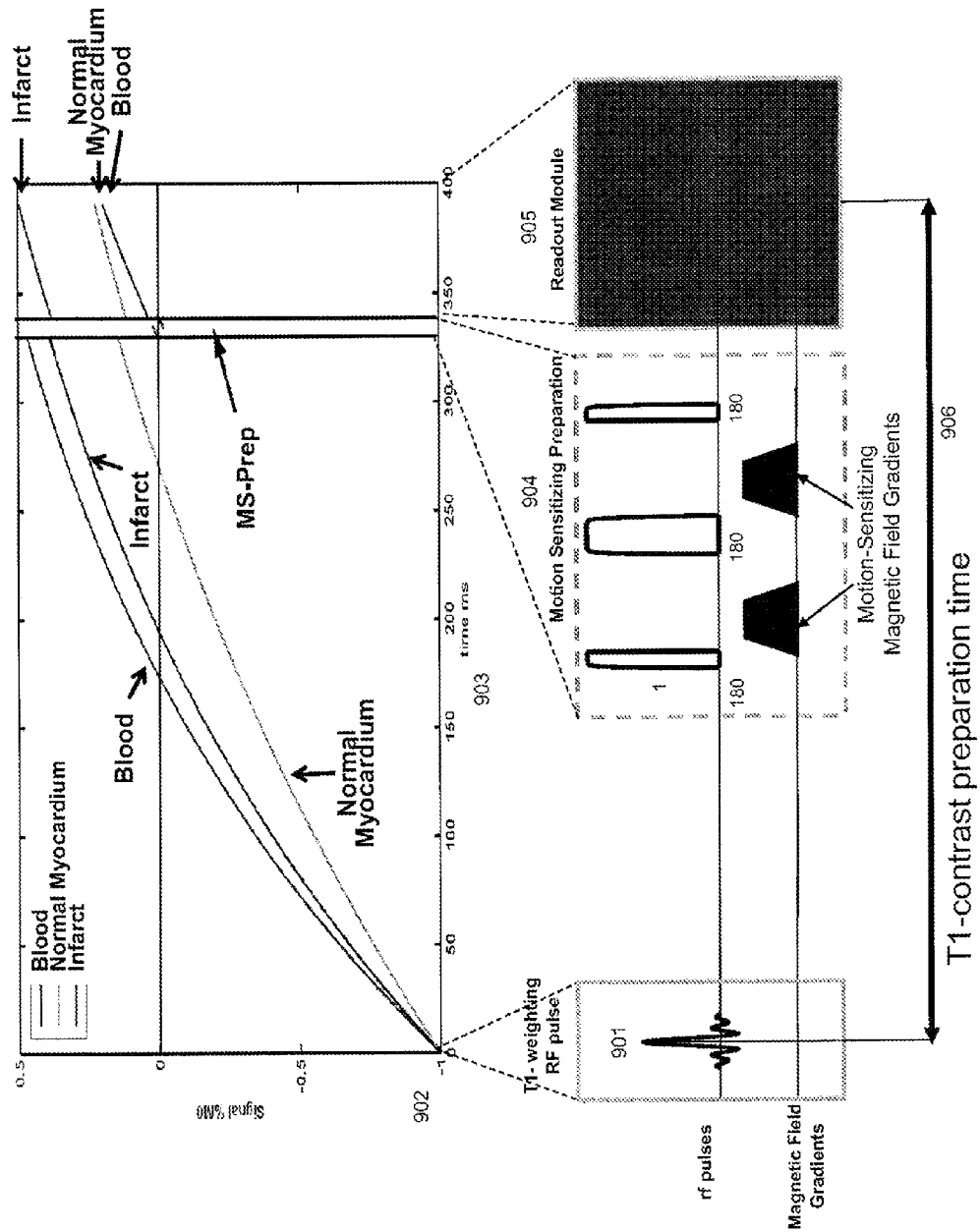
FIG. 9 illustrates a nuclear magnetic resonance preparation for imparting contrast weighting and concurrently attenuating a blood signal by dephasing the blood magnetization with motion-sensitization, according to one aspect of an embodiment of the present invention.

FIG. 9 illustrates a nuclear magnetic resonance preparation for imparting contrast weighting and concurrently attenuating a blood signal by dephasing the blood magnetization with motion-sensitization, to render the blood dark without requiring exchange of blood from the slice of interest or specific timing related to the relaxation parameters of the blood, according to one aspect of an embodiment of the present invention. In an embodiment for performing contrast-enhanced late gadolinium enhancement with dark-blood signal, as shown, a T1-weighting 180 degree RF pulse (901) is applied (this could be replaced with a partial inversion, or a saturation or partial saturation pulse without loss of generality). This inversion pulse inverts the sign of the magnetization in the heart muscle and cavity (902). After allowing a time for the magnetization to recover via longitudinal (T1 relaxation), the motion sensitizing preparation is applied (904). The motion sensitizing preparation converts the longitudinal magnetization into transverse magnetization, and preferentially dephases the transverse magnetization of the blood due to its inherent incoherent motion. As this preparation is not spatially selective, it will attenuate the signal from blood irrespective of the location of the blood relative to the imaging slice of interest without requiring exchange of blood out of the slice of interest. The final RF-pulse of the motion sensitizing preparation converts the transverse magnetization to longitudinal magnetization, which will then evolve based on the T1-properties of the blood, infarct, and normal myocardium, respectively, during the readout module (905). The total time for T1-preparation (906) is the time between the T1-weighting inversion pulse and the center of k-space for the readout module. As the motion sensitizing preparation is kept short in duration, it minimally affects the T1-recovery curve of normal myocardium and infarct.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

The following patents, applications and publications as listed below and throughout this document are hereby incorporated by reference in their entirety herein.

The devices, systems, compositions, computer program products, and methods of various embodiments of the invention disclosed herein may utilize aspects disclosed in the following references, applications, publications and patents and which are hereby incorporated by reference herein in their entirety:

1. Kim R J, Wu E, Rafael A, Chen E L, Parker M A, Simonetti O et al., "The Use of Contrast-Enhanced Magnetic Resonance Imaging to Identify Reversible Myocardial Dysfunction", N Engl J Med 2000; 343:1445-53.
2. Kim R J, Shah D J, "Fundamental Concepts in Myocardial Viability Assessment Revisited: When Knowing How Much Is "Alive" Is Not Enough", Heart 2004; 90:137-40.
3. Simonetti, OP, Finn, J P, Laub G, Henry D A, ""Black Blood" T2 Weighted Imaging of the Heart" Radiology 1996; 199:49-57.
4. Pell G S, Lewis D P, Branch C A, "Pulsed Arterial Spin Labeling Using TurboFLASH with Suppression of Intravascular Signal", Magn Reson. Med. 2003; 49:341-350.
5. Ibrahim E H, Weiss R G, Stuber M, Kraitchma D L, Li P, Spooner A E, Osman N F. "Stimulated-Echo Acquisition Mode (STEAM) MRI for Black-Blood Delayed Hyperenhanced Myocardial Imaging" J Magn Reson Imaging. 2008; 27:229-238.
6. Koktzoglou, I, Li D. "Diffusion-Prepared Segmented Steady-State Free Precession: Application to 3D Black-Blood Cardiovascular Magnetic Resonance of the Thoracic Aorta and Carotid Artery Walls" Journal of Cardiovasc Magn Reson. 2007; 9:1, 33-42.
7. Nguyen T D, de Rocheford L, Spincemaille P, Cham M D, Weinsaft J W, Prince M R, Wang Y. "Effective Motion-Sensitizing Magnetization Preparation for Black Blood Magnetic Resonance Imaging of the Heart", Journal of Magn Reson. Imaging; 2008; 28:1092-1100
8. Klem I, Heitner J F, Shah D J, Sketch M H, Jr., Behar V, Weinsaft J et al. "Improved Detection of Coronary Artery Disease By Stress Perfusion Cardiovascular Magnetic Resonance with the Use of Delayed Enhancement Infarction Imaging", J Am Coll Cardiol 2006; 47:1630-8.
9. Di Bella E V, Parker D L, Sinusas A J., "On The Dark Rim Artifact In Dynamic Contrast-Enhanced MRI Myocardial Perfusion Studies", Magn Reson Med 2005; 54:1295-9.
10. Ferreira P, Gatehouse P, Bucciarelli-Ducci C, Wage R, Firmin D. "Measurement of Myocardial Frequency Offsets During First Pass Of A Gadolinium-Based Contrast Agent In Perfusion Studies", Magn Reson Med 2008; 60:860-70.

11. Storey P, Chen Q, Li W, Edelman R R, Prasad P V. "Band Artifacts Due To Bulk Motion', Magn Reson Med 2002; 48:1028-36.
12. Dyverfeldt, et al., "Quantification of Intravoxel Velocity Standard Deviation and Turbulence Intensity by Generalizing Phase-Contrast", Magnetic Resonance in Imaging, 2006, 56:850-858.
13. Gao, et al., "Turbulent Flow Effects on NMR Imaging: Measurement of Turbulent Intensity", Med. Phys. 1991, 18 (5), 1045-1051.
14. Grant, et al., "NMR Rheotomography: Feasibility and Clinical Potential", Med. Phys. 1982, 9 (2), 188-193.
15. Sun, et al., "Comparison of Velocity-Encoded MR Imaging and Fluid Dynamic Modeling of Steady and Disturbed Flow", JMRI, 1982, 2:443-452.
16. Moran, P., "A Flow Velocity Zeugmatographic Interlace for NMR Imaging in Humans", Magnetic Resource Imaging 1982, 1: 197-203.
17. Lee, et al., "Diffusion Imaging with the MP-RAGE Sequence", JMRI, 1994, 837-842.
18. Abstract, "Diffusion/Diffusion II", JMRI, 1:2, 201-20312.
19. Coremans, et al., "A Comparison Between Different Imaging Strategies for Diffusion Measurements with the Centric Phase-Encoded Turbo-FLASH Sequence", J of Magnetic Resonance, 1977, 124: 323-342.
20. Sirol, et al., "Lipid-Rich Atherosclerotic Plaques Detedted by Gadofluorine-Enhanced in vivo Magnetic Resonance Imaging", Circ. Journal, 2004, 2890-2896.
21. Koktzoglou, "Multislice Dark-Blood Carotid Artery Wall Imaging: A 1.5 T and 3.0 T Comparison", JMRI, 2006, 699-705.
22. Lin, et al., "Rapid Dark-Blood Carotid Vessel-Wall Imaging with Random Bipolar Tradients in a Radial SSFP Acquisition", JMRI, 2007: 215:1299-1304.
23. Bornstedt, et al., "Local Excitation Black Blood Imaging at 3 T: Application to the Carotid Artery Wall", Magnetic Resonance in Medicine, 2008, 59:1207-1211.
24. U.S. Pat. No. 6,205,349 B1, Kim, et al., "Differentiating Normal Living Myocardial Tissue, Injured Living Myocardial Tissue, and Infarcted Myocardial Tissue in vivo Using Magnetic Resonance Imaging, Mar. 20, 2001.
25. U.S. Pat. No. 6,498,946 B1, Foo, et al., "Efficient Multi-Slice Acquisition with Black Blood Contrast", Dec. 24, 2002.
26. U.S. Pat. No. 6,526,307 B2, Foo, "Method and Apparatus to Improve Myocardial Infarction Detection with Blood Pool Signal Suppression", Feb. 27, 2003.
26. U.S. Pat. No. 6,662,037 B2, Foo, "Method and Apparatus to Improve Myocardial Infarction Detection with Blood Pool Signal Suppression", Dec. 9, 2003.
27. U.S. Pat. No. 7,369,887 B2, Fayad, et al., "Rapid Multi-slice Black Blood Double-Inversion Recovery Technique for Blood Vessel Imaging, May 6, 2008.
28. U.S. Patent Application Publication No. US 2009/0005673 A1, Rehwald, et al., "Dark Blood Delayed Enhancement Magnetic Resonance Viability Imaging Techniques for Assessing Subendocardial Infarcts", Jan. 1, 2009.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A method for magnetic resonance imaging of a heart of a subject, said method comprising:

administering a contrast agent to the subject;

applying a nuclear magnetic resonance preparation, comprising inversion rf-pulses, partial inversion rf-pulses, a saturation rf-pulse, or a partial saturation rf-pulse, to impart T1 contrast weighting to the myocardium of the heart;

applying a motion-sensitization gradient preparation, comprised of a plurality of rf-pulses and a plurality of magnetic field gradients and configured to dephase a signal corresponding to blood within the heart relative to a signal corresponding to the myocardium, based on the inherent motion of the blood in comparison to motion of the myocardium and independent of T1 relaxation properties of the blood and movement of the blood relative to an imaging plane prior to image acquisition, such that the blood is rendered dark relative to the myocardium; and reading out a nuclear magnetic resonance signal from the heart.

2. The method of claim 1, wherein the gradient motion-sensitization preparation comprises:
applying a 90 degree rf-pulse, a 180 degree rf-pulse, and a −90 degree rf-pulse; and
applying magnetic field gradients between the 90 and 180 and the 180 and −90 degree pulses to attenuate the signal corresponding to blood within the heart.

3. The method of claim 2, wherein the motion-sensitization preparation is applied using a composite rf-pulse structure.

4. The method of claim 1, wherein said reading out comprises gradient echo or gradient echo-train readout.

5. The method of claim 1, wherein said reading out comprises spin echo or turbo spin echo readout.

6. The method of claim 1, wherein said reading out comprises a combination of spin echoes and gradient echo readouts.

7. The method of claim 1, wherein said reading out comprises utilizing single-shot rapid imaging.

8. The method of claim 1, wherein said contrast agent is gadolinium based.

9. The method of claim 1, wherein the motion-sensitization preparation is configured to dephase the signal corresponding to the blood within the heart relative to the signal corresponding to the myocardium independent of location of the blood relative to the imaging plane during preparation or data acquisition.

10. A system for magnetic resonance imaging of a heart of a subject, said system comprising:
a data acquisition and display computer;
a control sequencer;
a MRI subsystem;
a contrast agent source configured to administer a contrast agent to the subject; and
a display;
wherein the control sequencer is programmed to:
apply a nuclear magnetic resonance preparation to impart T1 contrast weighting to the myocardium of the heart;
apply a motion-sensitization gradient preparation comprised of a plurality of rf-pulses and a plurality of magnetic field gradients configured to dephase a signal corresponding to a blood pool within the heart relative to a signal corresponding to the myocardium, based on the inherent motion of the blood in comparison to motion of the myocardium and independent of T1 relaxation properties of the blood and movement of the blood relative to an imaging plane prior to image acquisition, such that the blood pool is rendered dark relative to the myocardium; and
read out a nuclear magnetic resonance signal from the heart.

11. The system of claim 10, wherein the gradient motion-sensitization preparation comprises:
applying a 90 degree rf-pulse, a 180 degree rf-pulse, and a −90 degree rf-pulse; and
applying magnetic field gradients between the 90 and 180 and the 180 and −90 degree pulses to attenuate the signal corresponding to blood within the heart.

12. The system of claim 10, wherein said reading out comprises utilizing single-shot rapid imaging.

13. The system of claim 10, wherein said contrast agent is gadolinium based.

14. A method for magnetic resonance imaging of a heart of a subject, comprising:

administering a contrast agent to the subject;
applying a nuclear magnetic resonance preparation, to impart T1 contrast weighting to the myocardium of the heart;
applying a motion-sensitization gradient preparation configured to dephase a signal corresponding to a blood pool within the heart relative to a signal corresponding to the myocardium, based on the inherent motion of the blood in comparison to motion of the myocardium and independent of T1 relaxation properties of the blood and movement of the blood relative to an imaging plane prior to image acquisition, such that the blood pool is rendered dark relative to the myocardium; and
reading out a nuclear magnetic resonance signal from the heart.

15. The method of claim 14, wherein the gradient motion-sensitization preparation comprises:
applying a 90 degree rf-pulse, a 180 degree rf-pulse, and a −90 degree rf-pulse; and
applying magnetic field gradients between the 90 and 180 and the 180 and −90 degree pulses to attenuate the signal corresponding to blood within the heart.

16. The method of claim 15, wherein the motion-sensitization preparation is applied using a composite rf-pulse structure.

17. The method of claim 14, wherein said reading out comprises gradient echo or gradient echo-train readout.

18. The method of claim 14, wherein said reading out comprises spin echo or turbo spin echo readout.

19. The method of claim 14, wherein said reading out comprises a combination of spin echoes and gradient echo readouts.

20. The method of claim 14, wherein said reading out comprises utilizing single-shot rapid imaging.

21. The method of claim 14, wherein said contrast agent is gadolinium based.

22. A method for magnetic resonance imaging of a heart of a subject, said method comprising:
applying a nuclear magnetic resonance preparation to impart T2 or T2* contrast weighting to the myocardium of the heart;
applying a motion-sensitization gradient preparation configured to dephase a signal corresponding to a blood pool within the heart relative to a signal corresponding to the myocardium, based on the inherent motion of the blood in comparison to motion of the myocardium and independent of relaxation properties of the blood and movement of the blood relative to an imaging plane prior to image acquisition, such that the blood pool is rendered dark relative to the myocardium; and
reading out a nuclear magnetic resonance signal from the heart.

23. The method of claim 22, wherein the gradient motion-sensitization preparation comprises:
applying a 90 degree rf-pulse, a 180 degree rf-pulse, and a −90 degree rf-pulse; and
applying magnetic field gradients between the 90 and 180 and the 180 and −90 degree pulses to attenuate the signal corresponding to blood within the heart.

24. The method of claim 22 wherein the reading out of a nuclear magnetic resonance signal comprises playing out a readout module and the nuclear magnetic resonance signal comprises the signal attenuated by the motion-sensitization preparation.

25. The method of claim 22, wherein the motion-sensitization preparation is configured to dephase the signal corresponding to the blood within the heart relative to the signal corresponding to the myocardium independent of location of the blood relative to the imaging plane during preparation or data acquisition.

26. A system for magnetic resonance imaging of a heart of a subject, said system comprising:
   a data acquisition and display computer;
   a control sequencer;
   a MRI subsystem;
a display;
   wherein the control sequencer is programmed to:
      apply a nuclear magnetic resonance preparation comprised of a plurality of rf-pulses and a plurality of magnetic field gradients to impart T2 or T2* contrast weighting to the myocardium of the heart;
      apply a motion-sensitization gradient preparation comprised of a plurality of rf-pulses and a plurality of magnetic field gradients configured to dephase a signal corresponding to a blood pool within the heart relative to a signal corresponding to the myocardium, based on inherent motion of the blood in comparison to motion of the myocardium and independent of movement of the blood relative to an imaging plane prior to image acquisition, such that the blood pool is rendered dark relative to the myocardium; and
      read out a nuclear magnetic resonance signal from the heart.

* * * * *